United States Patent [19]

Krapcho et al.

[11] 4,173,634
[45] Nov. 6, 1979

[54] BASICALLY-SUBSTITUTED TRICYCLIC PYRAZOLES USEFUL AS ANTIINFLAMMATORY AGENTS

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 14,444

[22] Filed: Feb. 23, 1979

[51] Int. Cl.$^2$ ................ C07D 231/56; A61K 31/415
[52] U.S. Cl. .................... 424/248.4; 424/248.52; 424/248.58; 424/250; 424/267; 424/273 P; 544/140; 544/371; 546/199; 548/369
[58] Field of Search .............. 544/140, 371; 546/199; 548/369; 424/248.4, 248.52, 248.58, 250, 267, 273

[56] References Cited

U.S. PATENT DOCUMENTS 3,926,988  12/1975  Krapcho et al. ............ 544/140
3,969,527  7/1976   Krapcho et al. ............ 548/369

OTHER PUBLICATIONS

Hamilton, "J. Heterocyclic Chem.," vol. 13, (1976), pp. 545–553.

Primary Examiner—Alan L. Rotman
Assistant Examiner—R. W. Ramsuer
Attorney, Agent, or Firm—Lawrence S. Levinson; Burton Rodney

[57] ABSTRACT

Compounds of the structure

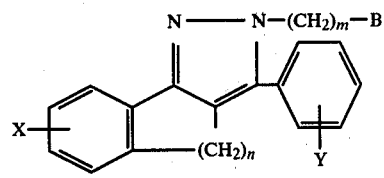

are provided, wherein n is 1, 2 or 3, m is 2, 3 or 4, X and Y may be the same or different and are hydrogen, halogen, lower alkyl, lower alkoxy, lower alkylthio or trifluoromethyl, and B is di-lower alkylamino, piperidino, pyrrolidino, morpholino, or N-lower alkylpiperazino and pharmaceutically acceptable acid-addition salts thereof. These compounds have been found to be useful as antiinflammatory agents.

13 Claims, No Drawings

BASICALLY-SUBSTITUTED TRICYCLIC PYRAZOLES USEFUL AS ANTIINFLAMMATORY AGENTS

DESCRIPTION OF THE INVENTION

The present invention relates to compounds of the structure

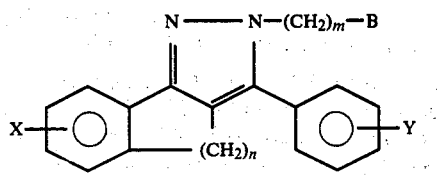

wherein n is 1, 2 or 3, m is 2, 3 or 4, X and Y may be the same or different and are H, halogen, preferably Cl or F, lower alkyl, lower alkoxy, trifluoromethyl or lower alkylthio, and B is di-lower alkylamino, piperidino, pyrrolidino, morpholino or N-lower alkylpiperazino and pharmaceutically acceptable acid-addition salts thereof.

In the above compounds, $(CH_2)_n$ represents a straight chain alkylene hydrocarbon group having from 1 to 3 carbons, such as $CH_2$, $(CH_2)_2$ or $(CH_2)_3$.

$(CH_2)_m$ represents a straight chain alkylene hydrocarbon group having from 2, 3 or 4 carbons, such as $(CH_2)_2$, $(CH_2)_3$, or $(CH_2)_4$.

Unless otherwise indicated, the term "lower alkyl" or "alkyl" as employed herein includes both straight and branched chain radicals of up to eight carbon atoms, preferably up to and including 5 carbon atoms, for instance, methyl, ethyl, n-propyl, isopropyl, n-butyl, t-butyl, isobutyl, n-pentyl, n-hexyl, 2,2,4-trimethylpentyl, and the like.

The terms "lower alkoxy" and "lower alkylthio" refer to any of the above "lower alkyl" groups attached to an oxygen or sulfur atom, respectively.

The term "halogen" refers to Cl, Br or F, with Cl or F being preferred.

The term "di-lower alkylamino" refers to groups of the structure

wherein $R^1$ and $R^2$ are the same or different and are each lower alkyl as defined above.

Preferred are those compounds of formula I wherein $(CH_2)_n$ is $CH_2$ or $(CH_2)_2$, $(CH_2)_m$ is $(CH_2)_3$, B is dilower alkylamino, X is hydrogen and Y is hydrogen or halogen.

The compounds of the invention may be prepared as follows.

A ketone of formula II wherein X, Y and n are as defined above

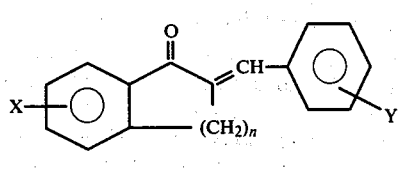

is oxidized to the corresponding epoxyketone III by reacting the formula II ketone with, for example, hydrogen peroxide in the presence of a lower alkanol solvent, such as methanol, and an alkali metal hydroxide according to the procedure described in J.A.C.S., 80, 900 (1958). The above procedure is carried out at a temperature of from about 25° to about 60° C., for a period of from about 1 to about 4 hours.

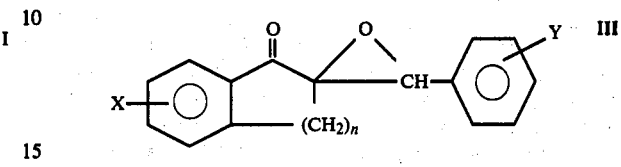

The epoxyketone III is then reacted with a hydrazine-lower alkyl-B compound IV $$H_2NNH(CH_2)_m B \qquad (IV)$$

in acid medium to produce the formula I compounds of the invention. The above reaction is carried out in the presence of a polar organic solvent, preferably lower alkanol, such as methanol or ethanol, and acid, such as glacial acetic acid, preferably at about the reflux temperature of the solvent, for from about 8 to about 30 hours.

The compounds of formula I form acid-addition salts by reaction with various inorganic and organic acids. These salts frequently provide convenient means for separating the product from the reaction mixture in which it is produced or from the solvent in which it is extracted in view of their insolubility in various media. Thus, the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acids salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The formula I compounds, as well as their acid-addition salts, have antiinflammatory activity as measured by the mouse active arthus (MAA) test and adjuvant arthritis test and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. For this purpose these compounds may be incorporated in a conventional dosage form such as tablet, capsule, injectable or the like, along with the necessary carrier material, excipient, lubricant, buffer or the like, as will be seen hereinafter, for oral or parenteral administration in single or divided doses of about 1 to 150 mg/kg/day, preferably about 5 to 75 mg/kg, two to four times daily.

The compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples represent preferred embodiments of the present invention.

EXAMPLE 1

4,5-Dihydro-N,N-dimethyl-3-phenyl-2H-benz[g]-indazole-2-propanamine, maleate salt (1:1)

A. 2-Benzylidene-1-tetralone oxide

Ten grams (0.043 mole) of 2-benzylidene-1-tetralone (prepared as described in U.S. Pat. No. 3,926,988) is dissolved in 650 ml of MeOH at 35°, stirred, and treated with 10.5 g (0.092 mole) of 30% $H_2O_2$, followed by 10.5 ml (0.042 mole) of 16% NaOH solution while maintaining the temperature at 35°–36°. After stirring for 4 hours at room temperature, the solution is concentrated to approximately 50 ml on a rotary evaporator (high vacuum, low heat), diluted with 250 ml of cold $H_2O$ (an oil separates), extracted with ether (200 ml; then 4×100 ml), the combined ether layers dried (MgSO$_4$), and the solvent evaporated to give 11.0 g (100%) of a semi-crystalline residue. Crystallization (of 10.6 g) from 55 ml of (i-Pr)$_2$O gives 8.3 g (80%) of colorless solid; m.p. 71°–73°. Lit m.p. 77°–77.5° [JACS, 79, 232 (1957)].

B.

4,5-Dihydro-N,N-dimethyl-3-phenyl-2H-benz[g]indazole-2-propanamine

A solution of the above epoxyketone (10.0 g; 0.04 mole) and 5.0 g (0.043 mole) of 3-dimethylaminopropylhydrazine in 160 ml of EtOH is treated with 6.3 ml of glacial acetic acid and refluxed for 24 hours. The light yellow solution is cooled, the bulk of solvent removed on a rotary evaporator, the oily residue shaken with 75 ml of $H_2O$ and 150 ml of ether, basified with excess $K_2CO_3$, and the layers separated. The aqueous phase is extracted with additional ether (3×75 ml), the combined ether layers dried (MgSO$_4$), and the solvent evaporated to give 13.1 g of a yellow-orange oil. The oil is redissolved in 150 ml of ether, and extracted with a cold solution of 3.5 ml of concentrated HCl in 125 ml of $H_2O$, followed by 2×50 ml $H_2O$. The combined aqueous layers are washed with some ether (wash discarded), layered over with 100 ml of ether, stirred, basified with 7 g of $K_2CO_3$, the layers separated, the aqueous phase extracted with ether (3×100 ml), the combined ether layers dried (MgSO$_4$), Darco-treated, and the solvent evaporated to give 9.1 g of a yellow oil. Crystallization from 40 ml of MeCN gives 4.9 g of a pale greyish solid; m.p. 60°–62° (s. 58°).

C.

4,5-Dihydro-N,N-dimethyl-3-phenyl-2H-benz[g]indazole-2-propanamine, maleate salt (1:1)

The above base (4.85 g) and 1.75 g of maleic acid are dissolved in 25 ml of warm MeCN and diluted with 110 ml of ether. On seeding and rubbing, the crystalline maleate salt rapidly separates. After cooling overnight, the colorless solid is filtered under N$_2$, washed with ether, and dried in vacuo; wt., 5.5 g; m.p. 106°–108°. The material is combined with 1.7 g of similar product from an earlier experiment and crystallized from 35 ml MeOH-320 ml ether to give 6.2 g of colorless solid; m.p. 106°–108°.

EXAMPLE 2

N,N-Dimethyl-3-phenylindeno[1,2-c]pyrazole-2(4H)-propanamine, hydrochloride (1:1)

A. 2-Benzylidene-1-indanone oxide

2-Benzylidene-1-indanone [3.3 g (0.015 mole), prepared as described in U.S. Pat. No. 3,926,988] is dissolved in 160 ml of MeOH and converted to the epoxide using 3.5 g (0.031 mole) of 30% $H_2O_2$ and 3.5 ml (0.014 mole) of 16% NaOH as described in Example 1 to give 3.2 g (90%) of colorless solid; m.p. 115°–117°. A sample crystallized from i-PrOH melts at 118°–120°. Lit m.p. 121°–122° [JACS, 80, 900 (1958)].

B.

N,N-Dimethyl-3-phenylindeno[1,2-c]-pyrazole-2(4H)-propanamine

The above epoxy ketone (3.1 g; 0.0131 mole) is reacted with 1.6 g (0.014 mole) of 3-dimethylaminopropylhydrazine in 55 ml of EtOH in the presence of 2.1 ml of glacial acetic acid as described in Example 1 (solution obtained at 50°) to give 4.2 g of oily residue. Following acid-base treatment as in Example 1, the yellow-orange viscous oily base weighs 3.6 g.

C.

N,N-Dimethyl-3-phenylindeno[1,2-c]-pyrazole-2(4H)propanamine, maleate salt

The base (3.4 g) and 1.25 g of maleic acid are dissolved in 20 ml of warm MeCN and diluted with 80 ml of ether. On seeding and rubbing, the crystalline maleate salt rapidly separates; wt., after cooling overnight, 4.0 g; m.p. 118°–120°. Following crystallization from 20 ml MeOH-130 ml ether, the light straw-colored solid weighs 3.3 g; m.p. 119°–121°.

D.

N,N-Dimethyl-3-phenylindeno[1,2-c]pyrazole-2(4H)-propanamine, hydrochloride (1:1)

The maleate salt is converted to the oily base and the latter (2.2 g) is dissolved in 15 ml of MeCOEt, cooled, and treated with 1.23 ml of 5.6 N alcoholic HCl. On rubbing, the crystalline HCl salt separates. Ether is added to complete the precipitation and after cooling overnight the material is filtered, washed with ether, and dried in vacuo; wt., 2.3 g; m.p. 166°–169° (s. 160°). Following crystallization from 40 ml of MeCN, the colorless solid weighs 1.7 g; m.p. 168°–170° (s. 166°).

EXAMPLE 3

3-(4-Chlorophenyl)-N,N-dimethylindeno[1,2-c]-pyrazole-2(4H)propanamine, hydrochloride (1:1)

A. 2-(p-Chlorobenzylidene)-1-indanone

A mixture of 100 g of indanone, 112 g of p-chlorobenzaldehyde and 500 ml of ethanol is stirred, the resulting solution is cooled to −10° and treated rapidly (3 minutes) with a solution of 5.0 g of KOH in 100 ml of ethanol. The solution is allowed to warm and the product begins to crystallize at 17° (cooled to keep under 15°). The resulting slurry is allowed to stir at 20°–25° for 1 hour, and then poured onto 2 liters of icewater. After standing for 3 hours, the solid is filtered, washed with cold water and allowed to air dry; wt., 190 g, m.p. 174°–179°. After crystallization from 400 ml of DMF, the cream-colored solid weighs 164.5 g (86%), m.p. 177°–179°.

B. 2-(p-Chlorobenzylidene)-1-indanone oxide

Ten grams (0.039 mole) of 2-(p-chlorobenzylidene)-1-indanone is converted to the epoxide in 1 liter of MeOH, using 9.6 g (0.085 mole) of 30% $H_2O_2$ and 9.6 ml (0.039 mole) of 16% NaOH, as described in Example 1. Since the starting material is poorly soluble in MeOH it is oxidized as a suspension and the product separates during the course of the reaction (5 hours at 35°–38°). The crude yield is 10 g (94%); m.p. 162°–164°. Crystallization (of 9.7 g) from 70 ml of MeCN gives 8.8 g (86%) of nearly colorless solid; m.p. 165°–167°.

C. 3-(4-Chlorophenyl)-N,N-dimethylindeno-[1,2-c]pyrazole-2(4H)-propanamine

The above epoxide (3.4 g; 0.0125 mole) is reacted with 1.55 g (0.0132 mole) of 3-dimethylaminopropylhydrazine in 60 ml of EtOH in the presence of 2.0 ml of glacial acetic acid as described in Example 1 to give 3.5 g of oily base.

D. 3-(4-Chlorophenyl)-N,N-dimethylindeno[1,2-c]pyrazole-2(4H)-propanamine, hydrochloride (1:1)

The oily base (3.3 g) is dissolved in 35 ml of MeCN, cooled, stirred and treated with 1.7 ml of 5.6 N alcoholic HCl; the solid HCl salt rapidly separates; wt., after cooling overnight, 2.9 g; m.p. 225°–227°. Following crystallization from 25 ml warm MeOH-75 ml ether, the colorless solid weighs 2.7 g; m.p. 226°–228°.

EXAMPLE 4

3-(4-Chlorophenyl)-N,N-dimethylindeno[1,2-c]-pyrazole-2(4H)-propanamine, methanesulfonate salt (1:1)

A solution of 4.9 g (0.0139 mole) of the free base, 3-(4-chlorophenyl)-N,N-dimethylindeno[1,2-c]pyrazole-2(4H)-propanamine, from Example 3C, in 25 ml of MeCN is treated with 1.35 g (0.0139 mole) of $MeSO_3H$ dissolved in 5 ml of MeCN. On seeding and rubbing, the crystalline mesylate salt separates; wt., after cooling overnight, 4.1 g (66%); m.p. 151°–153°. Following recrystallization from 20 ml of MeOH-100 ml ether, the cream-colored solid weighs 3.8 g (61%); m.p. 151°–153°.

EXAMPLE 5

3-(4-Chlorophenyl)-2,4-dihydro-2-[3-(4-morpholinyl)-propyl]indeno[1,2-c]pyrazole, hydrochloride (1:1)

Interaction of 16.1 g (0.059 mole) of 2-(p-chlorobenzylidene)-1-indanone oxide and 10.0 g (0.063 mole) of 3-morpholinopropylhydrazine in 285 ml of EtOH in the presence of 9.6 ml of glacial acetic acid as described in Example 1 yields 20.2 g of crude base as a yellow-orange viscous syrup. The latter is dissolved in 150 ml of warm MeCN, cooled, and treated with 9.3 ml of 5.5 N alcoholic HCl. After filtering a small amount of solid which has separated, the solution is diluted to 550 ml with ether. On rubbing, the crystalline HCl salt rapidly separates. After cooling overnight, the pale yellow solid weighs 20.1 g (78%); m.p. 174°–177° (s. 80°). Crystallization from 60 ml of MeCN gives 17.1 g of cream-colored material; m.p. 181°–183° (s. 140°). Following recrystallization from 60 ml of MeCN, the nearly colorless product weighs 13.7 g (53%); m.p. 181°–183°.

EXAMPLES 6 TO 16

Following the procedure of Example 1 but employing the 2-benzylidene-1-tetralone, shown in Column I of Table A set out below, and employing the hydrazine-lower alkyl-B compound shown in Column II, the product shown in Column III is obtained.

TABLE A

| | Column I | | Column II | Column III | | |
|---|---|---|---|---|---|---|
| | 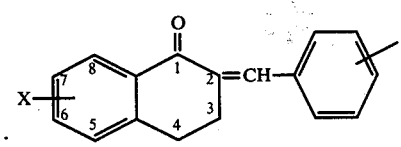 | | $H_2NNH(CH_2)_mB$ | 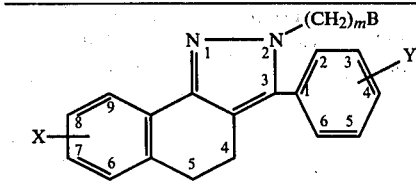 | | |
| Ex. No. | X(position) | Y(position) | $(CH_2)_mB$ | X(position) | Y(position) | $(CH_2)_mB$ |
| 6. | H | $CH_3(2)$ | $(CH_2)_3-N(C_2H_5)_2$ | H | as in Column I | as in Column II |
| 7. | H | $C_2H_5O(3)$ | $(CH_2)_3-N(C_3H_7)_2$ | H | | |
| 8. | H | $CF_3(4)$ | $(CH_2)_2-N(CH_3)(C_2H_5)$ | H | | |
| 9. | Cl(6) | H | $(CH_2)_4-N(CH_3)_2$ | Cl(7) | | |
| 10. | $CH_3(7)$ | Cl(4) | $(CH_2)_3-N(CH_3)_2$ | $CH_3(8)$ | | |
| 11. | $CH_3O(5)$ | H | $(CH_2)_2-N(C_2H_5)_2$ | $CH_3O(6)$ | | |
| 12. | $CF_3(6)$ | $CF_3(3)$ | $(CH_2)_3-N(CH_3)_2$ | $CF_3(7)$ | | |

TABLE A-continued

| | Column I | | Column II | Column III | | |
|---|---|---|---|---|---|---|
| Ex. No. | X(position) | Y(position) | H₂NNH(CH₂)ₘB (CH₂)ₘB | X(position) | Y(position) | (CH₂)ₘB |
| 13. | CH₃S(6) | H | (CH₂)₃—N piperidine | CH₃S(7) | as in Column I | as in Column II |
| 14. | H | F(4) | (CH₂)₃—N pyrrolidine | H | | |
| 15. | CH₃(6) | H | (CH₂)₂—N N—CH₃ (piperazine) | CH₃(7) | | |
| 16. | CH₃(5) | C₂H₅S(4) | (CH₂)₄—N N—C₂H₅ (piperazine) | CH₃(6) | | |

EXAMPLES 17 TO 27

Following the procedure of Example 1 but employing the ketone shown in Column I of Table B set out below, and employing the hydrazine-lower alkyl-B compound shown in Column II, the product shown in Column III is obtained.

TABLE B

| | Column I | | Column II | Column III | | |
|---|---|---|---|---|---|---|
| Ex. No. | X(position) | Y(position) | H₂NNH(CH₂)ₘB (CH₂)ₘB | X(position) | Y(position) | (CH₂)ₘB |
| 17. | H | CH₃(4) | (CH₂)₃—N(C₂H₅)₂ | H | as in Column I | as in Column II |
| 18. | H | C₂H₅O(3) | (CH₂)₃—N(C₃H₇)₂ | H | | |
| 19. | H | CF₃(4) | (CH₂)₂—N(CH₃)(C₂H₅) | H | | |
| 20. | Cl(5) | H | (CH₂)₄—N(CH₃)₂ | Cl(6) | | |
| 21. | CH₃(6) | Cl(2) | (CH₂)₃—N(CH₃)₂ | CH₃(7) | | |
| 22. | CH₃O(4) | H | (CH₂)₂—N(C₂H₅)₂ | CH₃O(5) | | |
| 23. | CF₃(5) | CF₃(4) | (CH₂)₃N(CH₃)₂ | CF₃(6) | | |
| 24. | CH₃S(6) | H | (CH₂)₃—N piperidine | CH₃S(7) | | |
| 25. | H | F(4) | (CH₂)₃—N pyrrolidine | H | | |
| 26. | CH₃(5) | H | (CH₂)₂—N N—CH₃ (piperazine) | CH₃(6) | | |

TABLE B-continued

| | Column I | Column II | | Column III | | |
|---|---|---|---|---|---|---|
| Ex. No. | X(position) | Y(position) | $H_2NNH(CH_2)_mB$ $(CH_2)_mB$ | X(position) | Y(position) | $(CH_2)_mB$ |
| 27. | $CH_3(4)$ | $C_2H_5S(4)$ | $(CH_2)_4-N\underset{\diagup}{\overset{\diagdown}{\phantom{x}}}N-C_2H_5$ | $CH_3(5)$ | as in Column I | as in Column II |

EXAMPLES 28 TO 38

Following the procedure of Example 1 but employing the ketone shown in Column I of Table C set out below, and employing the hydrazine-lower alkyl-B compound shown in Column II, the product shown in Column III is obtained.

wherein X and Y are the same or different and are H, halogen, lower alkyl, lower alkoxy, lower alkylthio, or trifluoromethyl, n is 1, 2 or 3, m is 2, 3 or 4, and B is dilower alkylamino, piperidino, pyrrolidino, morpholino, or N-lower alkylpiperazino, and pharmaceutically acceptable acid-addition salts thereof.

2. The compound according to claim 1 wherein n is 1.

TABLE C

| | Column I | | Column II | Column III | | |
|---|---|---|---|---|---|---|
| Ex. No. | X(position) | Y(position) | $H_2NNH(CH_2)_mB$ $(CH_2)_mB$ | X(position) | Y(position) | $(CH_2)_mB$ |
| 28. | H | $CH_3(4)$ | $(CH_2)_3-N(C_2H_5)_2$ | H | as in Column I | as in Column II |
| 29. | H | $C_2H_5O(3)$ | $(CH_2)_3-N(C_3H_7)_2$ | H | | |
| 30. | H | $CF_3(4)$ | $(CH_2)_2-N(CH_3)(C_2H_5)$ | H | | |
| 31. | Cl(7) | H | $(CH_2)_4-N(CH_3)_2$ | Cl(8) | | |
| 32. | $CH_3(8)$ | Cl(4) | $(CH_2)_3-N(CH_3)_2$ | $CH_3(9)$ | | |
| 33. | $CH_3O(6)$ | H | $(CH_2)_2-N(C_2H_5)_2$ | $CH_3O(7)$ | | |
| 34. | $CF_3(7)$ | $CF_3(4)$ | $(CH_2)_3N(CH_3)_2$ | $CF_3(8)$ | | |
| 35. | $CH_3S(6)$ | H | | $CH_3S(7)$ | | |
| 36. | H | F(4) | $(CH_2)_3-N\underset{\diagup}{\overset{\diagdown}{\phantom{x}}}$ | H | | |
| 37. | $CH_3(7)$ | H | $(CH_2)_3-N\underset{\diagup}{\overset{\diagdown}{\phantom{x}}}$ | $CH_3(8)$ | | |
| 38. | $CH_3(6)$ | $C_2H_5S(3)$ | $(CH_2)_2-N\underset{\diagup}{\overset{\diagdown}{\phantom{x}}}N-CH_3$ $(CH_2)_4-N\underset{\diagup}{\overset{\diagdown}{\phantom{x}}}N-C_2H_5$ | $CH_3(7)$ | | |

What is claimed is:

1. A compound of the formula

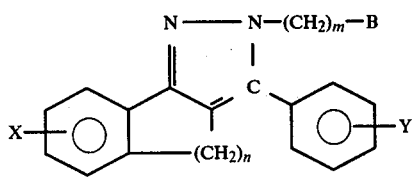

3. The compound according to claim 1 wherein n is 2.

4. The compound according to claim 1 wherein n is 3.

5. The compound according to claim 1 wherein B is dilower alkylamino.

6. The compound according to claim 1 wherein B is piperidino, pyrrolidino, morpholino, or N-lower alkylpiperazino wherein the alkyl radical has from 1 to 3 carbons.

7. The compound according to claim 1 wherein Y is hydrogen, Cl or F, and X is hydrogen.

8. The compound according to claim 1 having the name 4,5-dihydro-N,N-dimethyl-3-phenyl-2H-benz[g]indazole-2-propanamine or its maleate salt.

9. The compound according to claim 1 having the name N,N-dimethyl-3-phenylindeno[1,2-c]pyrazole-2(4H)-propanamine or its hydrochloride salt.

10. The compound according to claim 1 having the name 3-(4-chlorophenyl)-N,N-dimethylindeno[1,2-c]pyrazole-2(4H)-propanamine, its hydrochloride salt, or its methanesulfonate salt.

11. The compound according to claim 1 having the name 3-(4-chlorophenyl)-2,4-dihydro-2-[3-(4-morpholinyl)propyl]indeno[1,2-c]pyrazole-2(4H)-propanamine or its hydrochloride salt.

12. An antiinflammatory composition comprising an effective amount of a compound as defined in claim 1 and a pharmaceutically acceptable carrier therefor.

13. A method for treating an inflammatory condition, which comprises administering to a mammalian host an antiinflammatory amount of a compound as defined in claim 1.

* * * * *